(12) United States Patent
Pirc et al.

(10) Patent No.: US 8,592,474 B2
(45) Date of Patent: Nov. 26, 2013

(54) PROCESS FOR THE PREPARATION OR PURIFICATION OF OLMESARTAN MEDOXOMIL

(75) Inventors: Samo Pirc, Radovljica (SI); Lovro Selic, Celje (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 590 days.

(21) Appl. No.: 12/672,267

(22) PCT Filed: Aug. 7, 2008

(86) PCT No.: PCT/EP2008/060396
§ 371 (c)(1),
(2), (4) Date: Nov. 29, 2010

(87) PCT Pub. No.: WO2009/019303
PCT Pub. Date: Feb. 12, 2009

(65) Prior Publication Data
US 2011/0263666 A1  Oct. 27, 2011

(30) Foreign Application Priority Data

Aug. 8, 2007  (EP) .................................. 07114000
Aug. 8, 2007  (EP) .................................. 07114004

(51) Int. Cl.
*A61K 31/415*  (2006.01)
(52) U.S. Cl.
USPC ........................................................... 514/401
(58) Field of Classification Search
USPC ........................................................... 514/401
See application file for complete search history.

(56) References Cited

U.S. PATENT DOCUMENTS 5,616,599 A * 4/1997 Yanagisawa et al. ......... 514/381
2006/0281800 A1 12/2006 Kumar et al.

FOREIGN PATENT DOCUMENTS

| CA | 2 616 466 A1 | 2/2001 |
| CN | 1976926 A | 6/2007 |
| EP | 1801111 A1 | 6/2007 |
| EP | 1816131 A1 | 8/2007 |
| GB | 2419592 A | 5/2006 |
| WO | WO-2006/029056 A1 | 3/2006 |
| WO | WO-2007/017135 A2 | 2/2007 |
| WO | WO-2007/052301 A2 | 5/2007 |
| WO | WO-2007/115990 A1 | 10/2007 |
| WO | WO-2007/148344 A2 | 12/2007 |
| WO | WO-2008/043996 A2 | 4/2008 |

OTHER PUBLICATIONS

Hiroaki Yanagisawa, et al., "Nonpeptide Angiotensin II Receptor Antagonists: Synthesis, Biological Activities, and Structure—Activity Relationships of Imidazole-5-carboxylic Acids Bearing Alkyl, and Hydroxyalkyl Substituents at the 4-Position and Their Related Compounds", Journal of Medical Chemistry, 1996, pp. 323,338, vol. 39, No. 1, American Chemical Society.

(Continued)

*Primary Examiner* — San-Ming Hui
(74) *Attorney, Agent, or Firm* — Arent Fox LLP

(57) ABSTRACT

The present invention relates to a process for the preparation and purification of olmesartan medoxomil hydrohalide salts and optionally converting them to olmesartan medoxomil. The invention also relates to products obtainable by the process of the invention, to pharmaceutical compositions comprising the products and to their use in medicine, particularly to treat hypertension.

18 Claims, 12 Drawing Sheets

(56) References Cited

OTHER PUBLICATIONS

Yanagisawa et al., "Nonpeptide Angiotensin II Receptor Antagonists: Synthesis, Biological Activities, and Structure-Activity Relationships of Imidazole-5-Carboxylic Acids bearing Alkyl, Alkenyl, and Hydroxyalkyl Substituents at the 4-Position and Their Related Compounds", J. Med. Chem., 1996, 39 (1), pp. 323-338 (in English) (only ASC-Abstract available).

* cited by examiner

PROCESS FOR THE PREPARATION OR PURIFICATION OF OLMESARTAN MEDOXOMIL

CROSS-REFERENCE TO RELATED APPLICATION

This application is a 371 National Stage entry of International Application No. PCT/EP2008/060396, filed Aug. 7, 2008, now WO 2009/019303 with an International Publication date of Feb. 12, 2009, which claims the benefit of priority to EP 07114004.0, filed Aug. 8, 2007 and EP 07114000.8, filed Aug. 8, 2007, the entire specification, claims and drawings of which are incorporated herewith by reference.

FIELD OF THE INVENTION

The present invention is in the field of organic synthesis and relates to a process for the preparation and purification of olmesartan medoxomil hydrohalide salts and optionally converting them to olmesartan medoxomil. The invention also relates to products obtainable by the process of the invention, to pharmaceutical compositions comprising the products and to their use in medicine, particularly to treat hypertension.

BACKGROUND OF THE INVENTION

Olmesartan medoxomil is the name commonly given to (5-methyl-2-oxo-1,3-dioxol-4-yl)methyl 1-((2'-(1H-tetrazol-5-yl)biphenyl-4-yl)methyl)-4-(2-hydroxypropan-2-yl)-2-propyl-1H-imidazole-5-carboxylate, shown as (1) below. This chemical is known as an antagonist of angiotensin-II receptors and acts as an antihypertensive agent.

Scheme 1

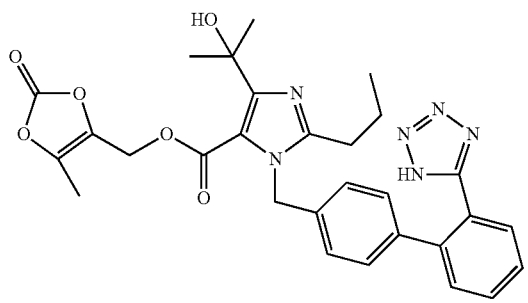

1

According to an article in *J. Med. Chem,* 1996, 39, 323-338 titled Nonpeptide Angiotensin II Receptor Antagonists, by Yanagisawa et al, olmesartan medoxomil is prepared as shown in the Scheme 2 below from the tritylated intermediate (2) by hydrolysis in aqueous acetic acid at elevated temperature in which triphenylmethanol is released.

Scheme 2

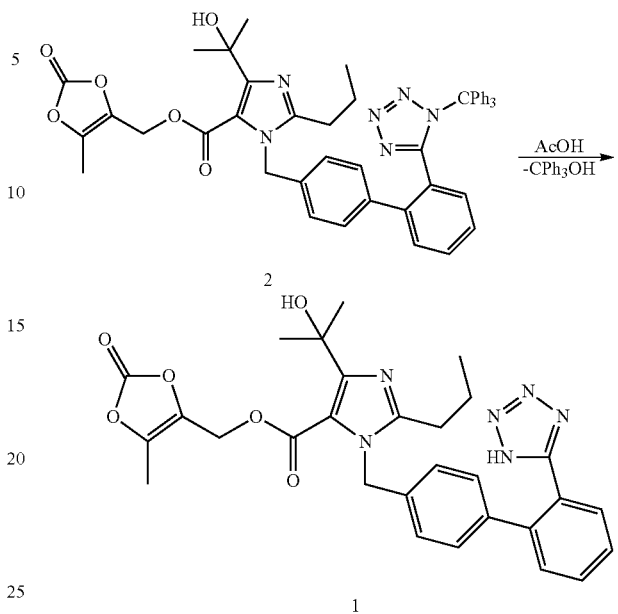

However, continued exposure to acidic conditions and the presence of water may lead to the cleavage of the ester bond to give olmesartan acid (3), as shown below (Scheme 3).

Scheme 3

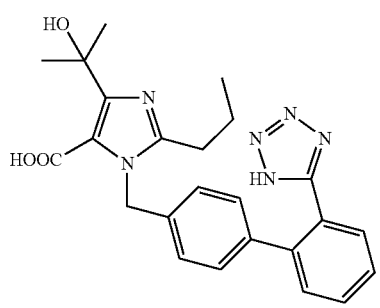

3

In addition to this degradation compound, the tritylated intermediate (2) would also contain impurities from previous steps.

WO 2007/017135 also discloses a method of making olmesartan medoxomil. In this method, the tritylated intermediate (2 as shown in scheme 2 above) is dissolved in acidic solution which causes deprotection to occur. The solution is then neutralised and olmesartan medoxomil is precipitated. The crude precipitated olmesartan medoxomil is then recrystallised to purify it.

There remains the need for an efficient way of preparing olmesartan medoxomil of high purity.

SUMMARY OF THE INVENTION

According to a first aspect, the present invention provides a process of preparing or purifying olmesartan medoxomil, the process comprising the steps of:

a) providing protected olmesartan medoxomil and forming a solution containing the protected olmesartan medoxomil and hydrohalic acid, thereby removing the protecting group; or b) forming a solution containing olmesartan medoxomil and hydrohalic acid; and c) forming olmesartan medoxomil hydrohalide salt in solid form and isolating the olmesartan medoxomil hydrohalide salt; and optionally d) converting the olmesartan medoxomil hydrohalide salt to olmesartan medoxomil.

According to a second aspect, the present invention provides an olmesartan medoxomil hydrohalide salt obtainable by a process according to the first aspect of the invention.

According to a third aspect, the present invention provides a pharmaceutical composition comprising olmesartan medoxomil hydrohalide salt according to the second aspect of the invention and a pharmaceutically acceptable carrier.

According to a fourth aspect, the present invention relates to the use of a olmesartan medoxomil hydrohalide salt according to the second aspect of the invention as a medicine, preferably to treat hypertension.

According to another aspect, the present invention relates to the use of olmesartan medoxomil hydrohalide salt according to the second aspect of the invention in preparing olmesartan medoxomil.

In general, the present invention is directed to a process for preparing or purifying olmesartan medoxomil (1) via isolation of the hydrohalide salt (1x, shown below in scheme 4):

Scheme 4

1x in which X means Cl, Br or I.

It is essential in the main embodiment that a hydrohalide salt of olmesartan medoxomil is isolated. Hydrohalide salts of olmesartan medoxomil are less soluble in water than in organic solvents and are more soluble in organic solvents than the olmesartan medoxomil itself, which is unusual. As a result of this, the hydrohalide salts can be easily isolated from water-rich mixtures of water and organic solvent by reducing the amount of organic solvent to form the salt in solid form.

The hydrohalide olmesartan medoxomil salts that are isolated according to the method of the invention have a well defined crystalline structure. This is in contrast to other olmesartan salts such as those formed with sulphate, nitrate, or acetate which are not in crystalline form and appear as thick oils, gum-like materials or do not precipitate at all.

A hydrohalic acid is used in the method of the invention which is preferably hydrochloric acid, hydrobromic acid or hydroiodic acid, more preferably hydrochloric acid or hydrobromic acid and most preferably hydrobromic acid. This forms the corresponding hydrohalide salt which is isolated.

The crystalline properties of the salt are most apparent in the hydrobromide salt, then the hydrochloride salt and then the hydroiodide salt.

As salts possess different physico-chemical properties from bases, crystallisation of olmesartan medoxomil hydrohalide salt removes more impurities than crystallisation of olmesartan medoxomil itself, especially if the impurities are not bases or have essentially different pK values. Therefore the preparation or purification of olmesartan medoxomil via the hydrohalide salts is a powerful tool for obtaining olmesartan medoxomil of high purity suitable for use in pharmaceutical applications.

There are different ways in which the olmesartan medoxomil hydrohalide salt can be prepared. The different ways of preparing olmesartan medoxomil hydrohalide salt affect the product obtained in the sense that different polymorphs are obtained, as described below.

FIGURES

DETAILED DESCRIPTION OF THE INVENTION

Figure 1:
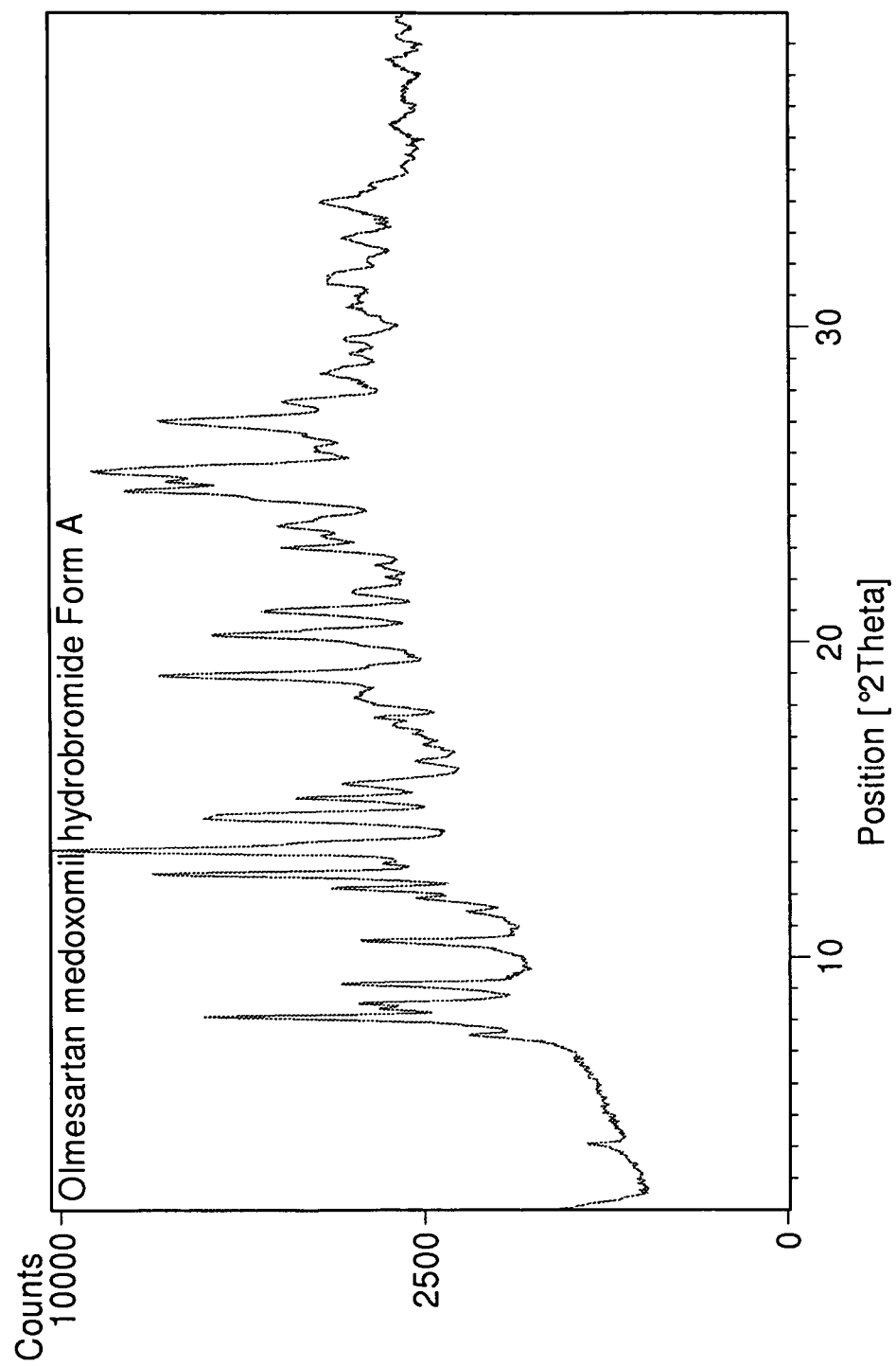
FIG. 1 is an X-ray powder diffraction spectrum of olmesartan medoxomil hydrobromide Form A.

The aspects, advantages, features and preferred embodiments of the present invention summarized in the following independent and preferred items, respectively alone or in combination, further contribute to solving the object of the invention:

(1) A process of preparing or purifying olmesartan medoxomil, the process comprising the steps of:

a) providing protected olmesartan medoxomil and forming a solution containing the protected olmesartan medoxomil and hydrohalic acid, thereby removing the protecting group; or b) forming a solution containing olmesartan medoxomil and hydrohalic acid; and c) forming olmesartan medoxomil hydrohalide salt in solid form and isolating the olmesartan medoxomil hydrohalide salt; and optionally d) converting the olmesartan medoxomil hydrohalide salt to olmesartan medoxomil.

(2) The process according to (1), wherein the hydrohalic acid is hydrochloric acid, hydrobromic acid or hydroiodic acid, preferably hydrochloric acid or hydrobromic acid, most preferably hydrobromic acid, and the hydrohalide salt in step c) if is formed from the hydrohalic acid in step a) or b).

(3) The process according to (1) or (2), wherein the solution containing hydrohalic acid in step a) or b) comprises a mixture of one or more water miscible organic solvents and water, and the water miscible organic solvent is partially or completely removed from the solution to cause formation of olmesartan medoxomil hydrohalide salt in step c).

(4) The process according to (3), wherein the water miscible organic solvent is selected from the group consisting of a $C_1$ to $C_6$ alcohol, a $C_1$ to $C_6$ ketone, a $C_1$ to $C_6$ nitrile, a $C_1$ to $C_6$ amide, a $C_1$ to $C_6$ ether, dimethyl sulfoxide, or mixtures thereof, wherein the water miscible organic solvent preferably comprises acetone, acetonitrile, ethanol, t-butanol, tetrahydrofuran, or 1,4-dioxane and most preferably comprises acetone.

(5) The process according to (1) or (2), wherein the solution containing hydrohalic acid in step a) or b) comprises tetrahydrofuran, and the solution is cooled and/or an antisolvent is added to cause formation of olmesartan medoxomil hydrohalide salt in step c).

(6) The process according to any preceding item, additionally comprising the step of purifying the olmesartan medoxomil hydrohalide salt obtained in step c) by dissolving it in tetrahydrofuran and forming the olmesartan medoxomil hydrohalide salt by cooling and/or adding an antisolvent to the solution.

(7) The process according to any preceding item, additionally comprising manufacturing of a pharmaceutical composition.

(8) An olmesartan medoxomil hydrohalide salt obtainable by a process according to items (1) to (6).

(9) Olmesartan medoxomil hydrobromide form A, having an X-ray diffraction pattern which includes 2-theta values at about: 8.1, 12.6, 13.3, 14.3, 18.9, 25.3, IR spectrum which includes representative peaks at about 1138, 930, 820, 763, 708 $cm^{-1}$, and a melting point with onset of about 81° C. and peak value of about 87° C.

10. Olmesartan medoxomil hydrochloride form A, having an X-ray diffraction pattern which includes 2-theta values at about 10.3, 10.8, 14.9, 16.3, 24.0, 25.4, an IR spectrum which includes representative peaks at about 1819, 1493, 1395, 1380, 1375, 1360, 1333, 1316, 1137, 1010, 940, 918, 878, 526 $cm^{-1}$, a melting point of about 125° C. and a degradation point of about 139° C.

(11) Olmesartan medoxomil hydrobromide form B, having an X-ray diffraction pattern which includes 2-theta values at about: 7.5, 10.5, 20.3, 21.6, 22.7, 24.3, an IR spectrum which includes representative peaks at about 1145, 922, 831, 768, 704, 690 $cm^{-1}$, and a DSC thermogram with endothermic peak of desolvatation at about 56° C. and endothermic peak of melting with decomposition at about 83° C.

(12) Olmesartan medoxomil hydrochloride form B, having an X-ray diffraction pattern which includes 2-theta values at about 7.5, 9.7, 12.8, 17.2, 21.7, 22.6, an IR spectrum which includes representative peaks at about 1826, 1502, 1386, 1365, 1331, 1145, 1006, 950, 923, 517 $cm^{-1}$, and a DSC thermogram with endothermic peak of desolvatation about 49° C. and endothermic peak of melting with decomposition at about 80° C.

(13) A pharmaceutical composition comprising olmesartan medoxomil hydrohalide salt according to any of items (8) to (12) and a pharmaceutically acceptable carrier.

(14) Use of olmesartan medoxomil hydrohalide salt according to any of (8) to (12) as a medicine, preferably to treat hypertension.

(15) Use of olmesartan medoxomil hydrohalide salt according to any of (8) to (12) in preparing olmesartan medoxomil.

(16) A process of preparing or purifying olmesartan medoxomil, wherein hydrohalic acid is used in concentrations from 10 wt-% or above.

(17) The process according to (16), wherein hydrohalic acids are used in concentrations from 20 wt-% or above.

(18) The process of according to (16) or (17), wherein concentrated acids are used in concentrations from 30 wt-% or above, preferably 48 wt-% or 62 wt-% hydrobromic acid or 35-38 wt-% hydrochloric acid, more preferably 48 wt-% hydrobromic acid.

(19) The process according to any of (1) to (7), wherein the step according to (1) a) is carried out at temperatures from 20° C. to reflux preferably from 25 to 30° C.

(20) The process according to (19), wherein the deprotection reaction is detritylation.

(21) The process according to (4), wherein the organic solvent to water ratio is preferably between 10:1 and 1:4 by volume, more preferably between 4:1 and 1:1 by volume.

(22) The process according to (1) d), wherein the mixture of at least one water miscible solvent and water is used.

(23) The process according to (22), wherein acetone, acetonitrile, lower alcohols, tetrahydrofuran, 1,4-dioxane, dimethyl sulfoxide, N,N-dimethylformamide, or N,N-dimethylacetamide, preferably lower alcohols, acetone or acetonitrile, most preferably acetone is used.

(24) The process according to (22) or (23), wherein the organic solvent to water ratio is between 2:1 and 1:3 by volume, preferably about 1:2 by volume.

(25) The process according to (22) to (24), wherein aqueous solution of inorganic base selected from alkali and alkaline earth carbonates, hydrogen carbonates, hydroxides, and alkoxides, preferably hydrogen carbonates, more preferably $NaHCO_3$ is added.

(26) A process of preparing a pharmaceutical composition comprising olmesartan medoxomil hydrohalide salt according to any of items (8) to (12), comprising mixing olmesartan medoxomil hydrohalide salt according to any of items (8) to (12) and a pharmaceutically acceptable carrier.

(27) A tablet comprising olmesartan medoxomil hydrohalide salts according to any of (8) to (12) or olmesartan medoxomil obtainable by the process according to (1).

In main embodiments of the invention, the method involves forming a solution containing olmesartan medoxomil which may be in a protected form and hydrohalic acid. This can be achieved either by forming a solution of hydrohalic acid and dissolving the olmesartan medoxomil, which may be protected, in it, or by dissolving the olmesartan medoxomil (optionally protected) in a solvent and then adding hydrohalic acid, which can be in the form of a liquid or gas.

Where olmesartan medoxomil is being prepared in the method, the olmesartan medoxomil is in protected form and dissolving the protected olmesartan medoxomil in a solution containing hydrohalic acid causes removal of the protecting group. Where the method is one of purification, olmesartan medoxomil itself is dissolved in the solution containing hydrohalic acid. In both methods olmesartan medoxomil in a form of hydrohalide salt arises, which can be optionally converted to olmesartan medoxomil.

The protected olmesartan medoxomil that can be used in step a) of the method of the invention may be provided from any source, and can be made by known methods, such as those described in WO 2007/017135.

A preferred way of providing protected olmesartan medoxomil is using a one-pot process with steps i) alkylating ethyl 4-(1-hydroxy-1-methylethyl)-2-propylimidazole-5-carboxylate (4) with 4-[2-(trityltetrazol-5-yl)phenyl]benzyl bromide (5) in an organic solvent, in the presence of a base, to produce trityl olmesartan ethyl ester (6), ii) hydrolysing the trityl olmesartan ethyl ester (6) in an organic solvent, in the presence of a base, to form trityl olmesartan salt (7), and iii) esterifying the trityl olmesartan salt (7) with 4-chloromethyl-5-methyl-1,3-dioxolene-2-one (8) in an organic solvent, in the presence of a base, to form trityl olmesartan medoxomil (2), as shown below in scheme 5.

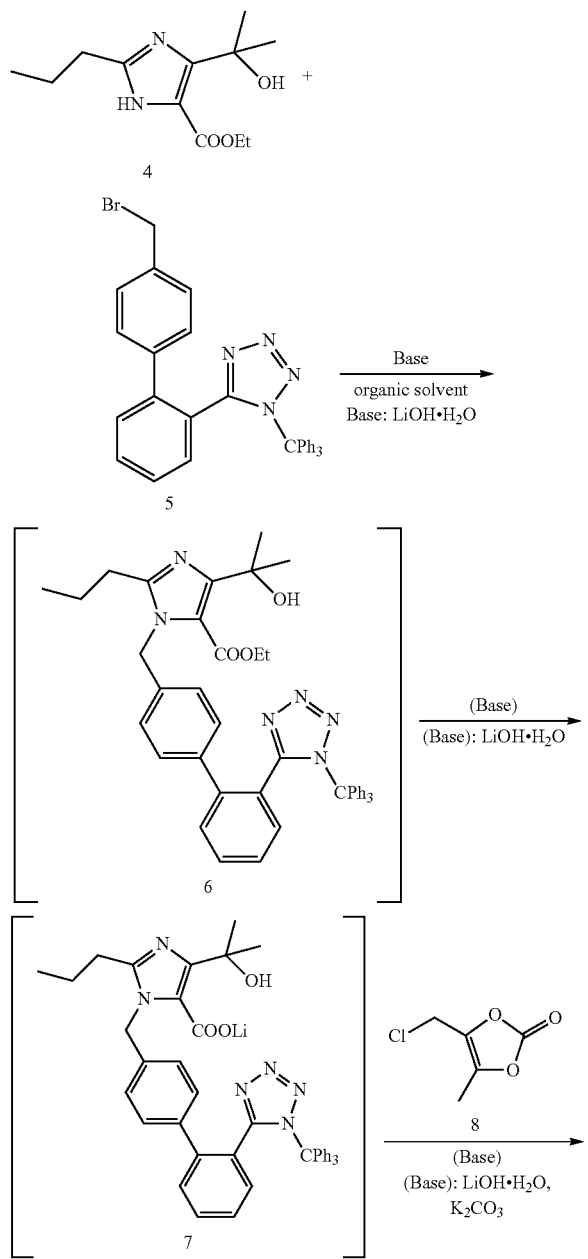

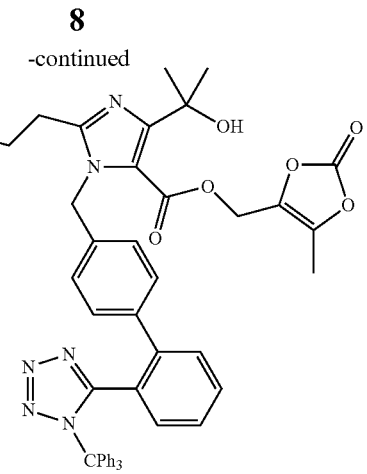

In the preferred embodiment, the same type of organic solvent is used in each of steps i) to iii), preferably wherein the organic solvent is N,N-dimethylacetamide. Preferably the same type of base is used in each of steps i) to iii), preferably wherein the base is lithium hydroxide hydrate.

Using a one-pot process is a simple and cost effective method of organic synthesis but is only commercially valuable where the level of impurities can be minimised to give a reasonable yield. Hence, a further advantage of the present invention, which gives an improved method of obtaining pure olmesartan from trityl olmesartan medoxomil, is that a one-pot process can be used to make the trityl olmesartan medoxomil.

In a first embodiment of the invention, the solution containing hydrohalic acid comprises a mixture of one or more water miscible organic solvents and water. The water miscible organic solvent is preferably selected from the group consisting of a $C_1$ to $C_6$ alcohol, a $C_1$ to $C_6$ ketone, a $C_1$ to $C_6$ nitrile, a $C_1$ to $C_6$ amide, a $C_1$ to $C_6$ ether, dimethyl sulfoxide, or mixtures thereof, wherein the water miscible organic solvent preferably comprises acetone, acetonitrile, ethanol, t-butanol, tetrahydrofuran, or 1,4-dioxane and most preferably comprises acetone.

The water miscible organic solvent is partially or completely removed from the solution to cause formation of olmesartan medoxomil hydrohalide salt.

Hydrohalic acids are preferably used as water solutions in concentrations from 10 wt-% or above, most preferably concentrated acids like 48 wt-% or 62 wt-% hydrobromic acid or 35-38 wt-% hydrochloric acid. 48 wt-% hydrobromic acid is the most preferable. The organic solvent to water ratio is preferably between 10:1 and 1:4 by volume, more preferably between 4:1 and 1:1 by volume.

Where the method is for the preparation of olmesartan medoxomil, a protected olmesartan medoxomil is used or first formed. The protecting group may be any commonly used protecting groups, for example tributylstannyl, alkyl, arylalkyl, diarylalkyl or triarylalkyl, such as t-Bu or diphenylethyl. Preferably the protecting group is triphenylmethyl (abbreviation trityl). In this case the protected olmesartan medoxomil is (5-methyl-2-oxo-1,3-dioxol-4-yl)methyl 1-((2'-(1H-tetrazol-5-yl)biphenyl-4-yl)methyl)-4-(2-hydroxypropan-2-yl)-2-propyl-1H-imidazole-5-carboxylate carrying triphenylmethyl protecting group on the tetrazole ring. Detritylation of the trityl olmesartan medoxomil occurs by use of hydrohalic acid in media which dissolve olmesartan medoxomil and olmesartan medoxomil hydrohalide salt but precipitate triphenylmethanol if additional water is added. Triphenylmethanol is then removed by filtration.

In this first embodiment, the hydrohalide salts precipitated have form A, which is discussed further below.

In a second embodiment, the solution containing hydrohalic acid in which the optionally protected olmesartan medoxomil is dissolved comprises tetrahydrofuran. The solution is cooled and/or an antisolvent is added to cause formation of olmesartan medoxomil hydrohalide salt.

In this case, the deprotection, preferably detritylation reaction is carried out at temperatures from 20° C. to reflux preferably from 25 to 30° C., and isolation is performed by cooling to −10 to 5° C. preferably to around 0° C. The hydrohalic acids are preferably used as water solutions as described above.

Alternatively or in addition to the decrease in temperature, an antisolvent is added to cause formation wherein the antisolvent is preferably selected from aromatic or aliphatic hydrocarbons and acyclic ethers, particularly preferably acyclic ethers, most preferably diisopropylether.

In this, the second embodiment, the olmesartan medoxomil salt is isolated in the form of a tetrahydrofuran (THF) solvate. This is form B, which is discussed further below.

In either embodiment, the olmesartan medoxomil hydrohalide salt isolated is surprisingly pure. If desired, it can be further purified by dissolving it in tetrahydrofuran and recrystallising the olmesartan medoxomil hydrohalide salt by cooling and/or adding an antisolvent to the solution. The olmesartan medoxomil hydrohalide salt is converted to olmesartan medoxomil by dissolving it in an acidic solution, then raising the pH of the solution to be between 5 and 8, at which point olmesartan medoxomil precipitates. The method of the invention can result in olmesartan medoxomil (1 in scheme 1) with purity greater than 99.7%. This can optionally be recrystallised, preferably from acetonitrile.

In more detail, in a preferred method according to the first embodiment of the invention, trityl olmesartan medoxomil (2 in scheme 2) is added to a mixture of at least one water miscible organic solvent and water. Acetone is the most preferred. The organic solvent to water ratio is preferably between 10:1 and 1:4 by volume, more preferably between 4:1 and 1:1 by volume. To this mixture hydrohalic acid HX is added, preferably HBr or HCl. Hydrohalic acid may be added as an aqueous solution or gas, preferably as a concentrated aqueous solution. Preferably, the amount of acid added is between 2 and 10 molar equivalents, more preferably between 3 and 4 equivalents, most preferably about 3 equivalents. The temperature at which the reaction is performed can be in range from −10 to 50° C., more preferably from 20 to 30° C. The mixture is stirred for 1 to 16 hours, preferably 2 to 4 hours.

Prior to separating the precipitated triphenylmethanol, water is added to the mixture to change the organic solvent to water ratio to about 1:3 to about 1:5, preferably to about 1:4. Triphenylmethanol is subsequently separated from the solution by any means known in the art, such as centrifugation or filtration.

The filtrate is concentrated to completely or partially remove organic solvents and the resulting aqueous suspension is stirred at temperatures ranging from 0° C. to room temperature to achieve maximum yield, then filtered to collect olmesartan medoxomil hydrohalide salt.

Figure 2:
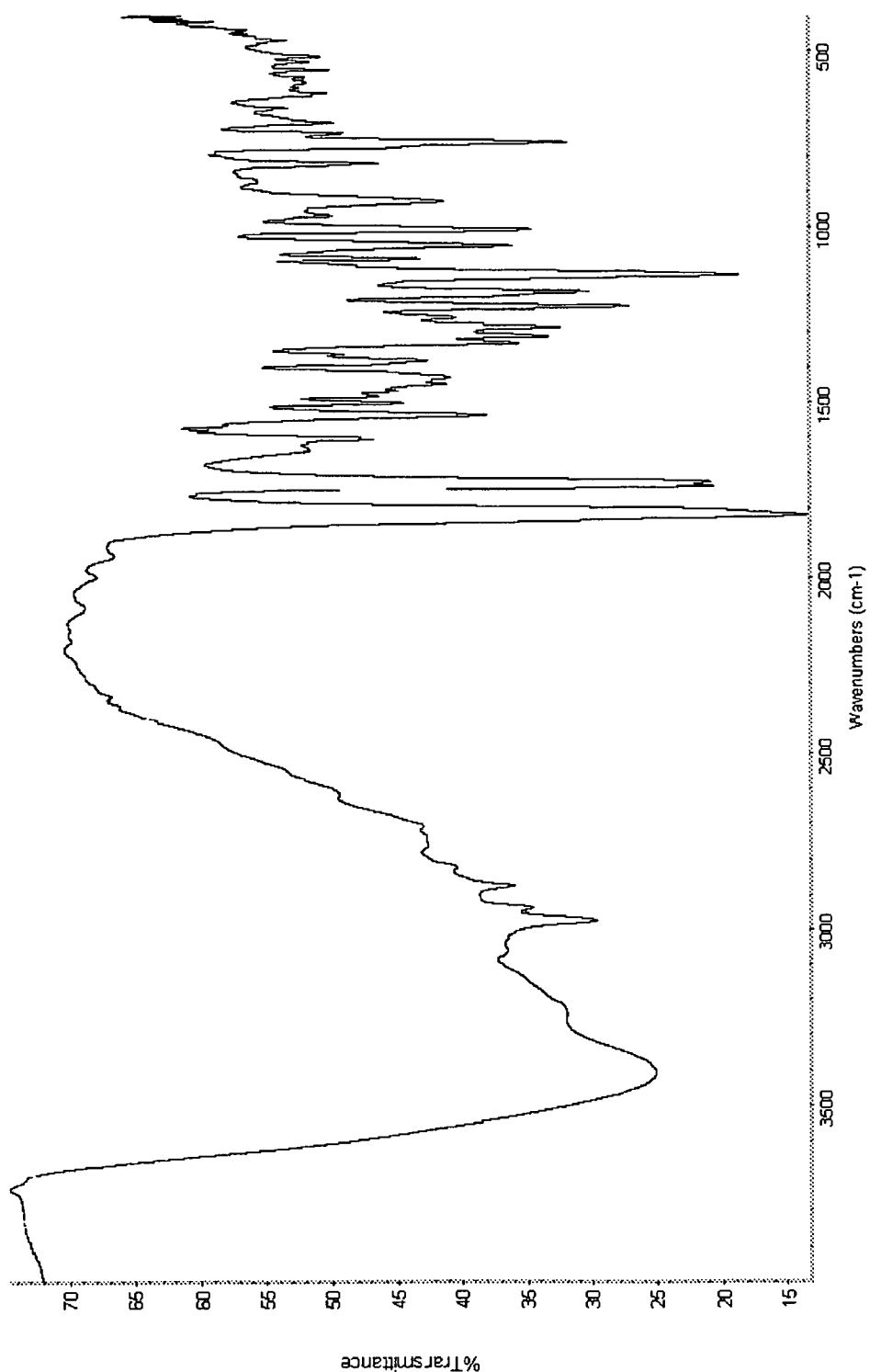
FIG. 2 is an IR spectrum of olmesartan medoxomil hydrobromide Form A.
Figure 3:
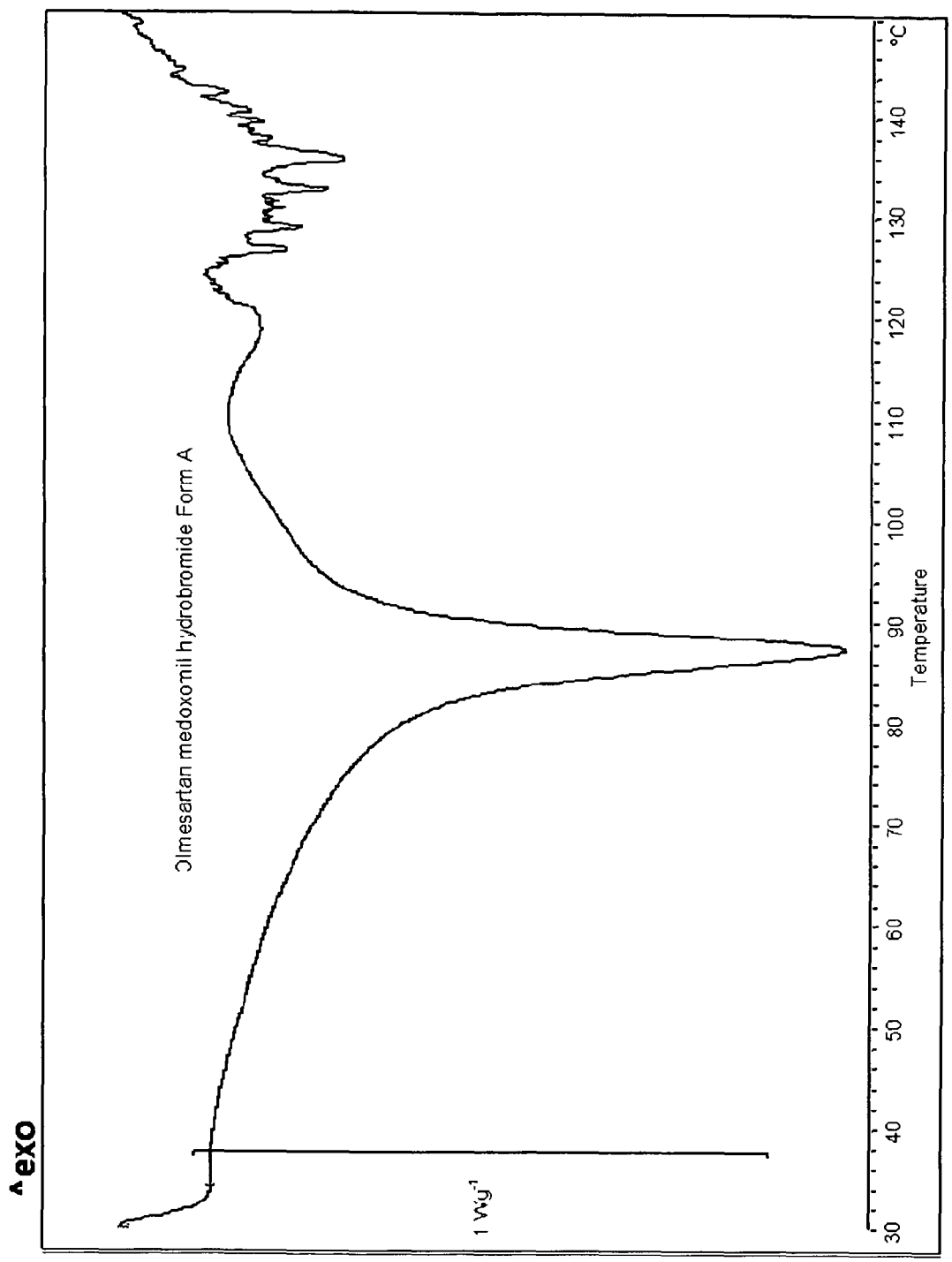
FIG. 3 is a DSC thermogram of olmesartan medoxomil hydrobromide Form A.

The olmesartan medoxomil hydrohalide salt which has precipitated from water or aqueous solution is in form A. Olmesartan medoxomil hydrobromide form A, precipitated from water or aqueous solution, is characterized by the diffractions in X-ray diffraction pattern substantially as in FIG. 1 at following 2-theta values in particular: 8.1, 12.6, 13.3, 14.3, 18.9, 25.3. It is also characterized by an IR spectrum as in FIG. 2 having representative peaks at about 1138, 930, 820, 763, 708 cm$^{-1}$. It is also characterized by a DSC thermogram as in FIG. 3 showing broad endothermic peak corresponding to melting with decomposition with onset temperature of about 81° C. and peak value of about 87° C.

Figure 7:
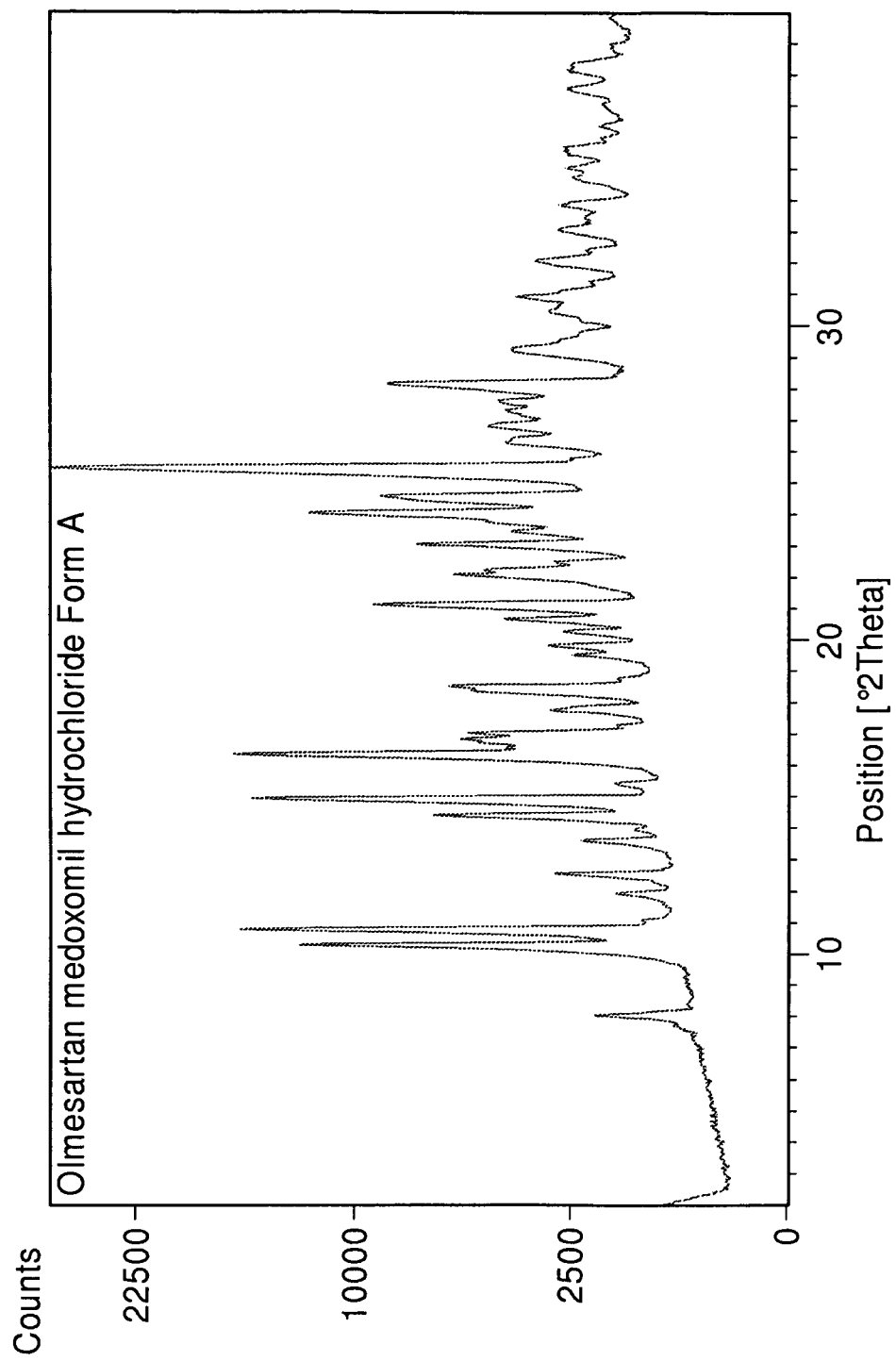
FIG. 7 is an X-ray powder diffraction spectrum of olmesartan medoxomil hydrochloride Form A.
Figure 8:
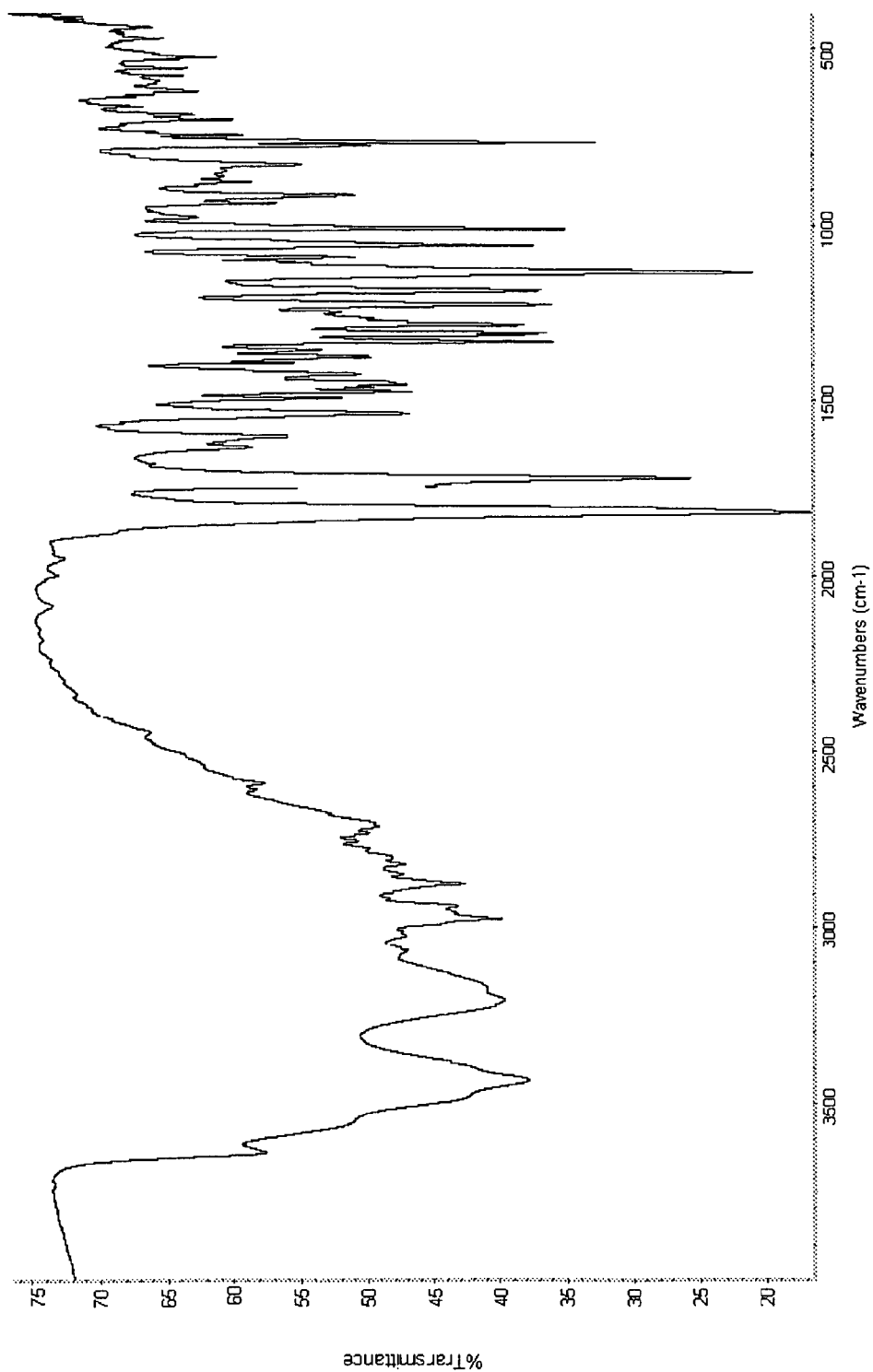
FIG. 8 is an IR spectrum of olmesartan medoxomil hydrochloride Form A.
Figure 9:
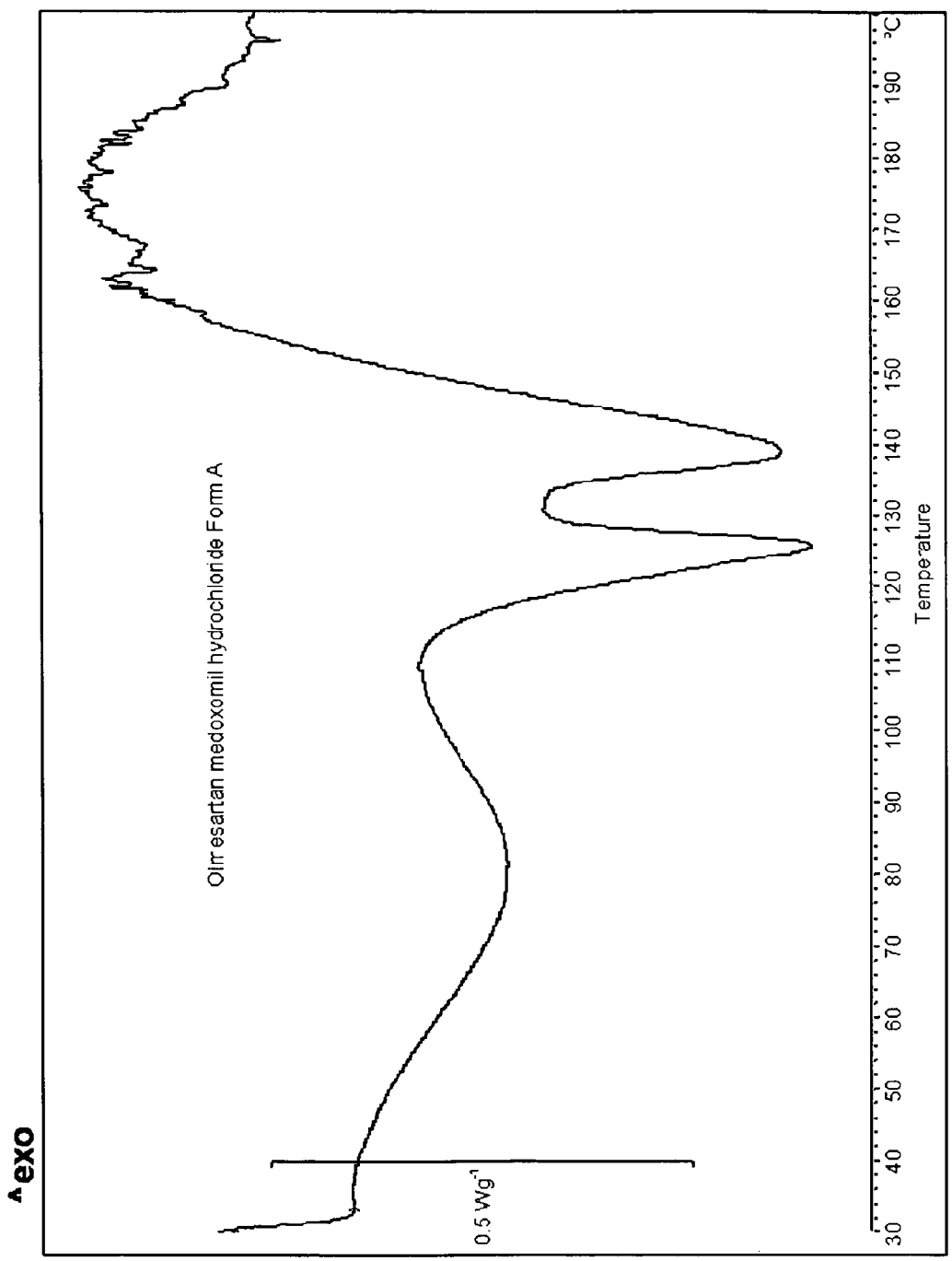
FIG. 9 is a DSC thermogram of olmesartan medoxomil hydrochloride Form A.

Olmesartan medoxomil hydrochloride form A precipitates from water or aqueous solution. It is characterized by the diffractions in X-ray diffraction pattern substantially as in FIG. 7 at following 2-theta values in particular: 10.3, 10.8, 14.9, 16.3, 24.0, 25.4. It is also characterized by an IR spectrum as in FIG. 8 having representative peaks at about 1819, 1493, 1395, 1380, 1375, 1360, 1333, 1316, 1137, 1010, 940, 918, 878, 526 cm$^{-1}$. It is also characterized by a DSC thermogram as in FIG. 9 showing two characteristic peaks at about 125° C. and about 139° C., which correspond to melting and degradation.

In more detail, in a preferred method according to the second embodiment of the invention, trityl olmesartan medoxomil is dissolved in THF, and hydrohalic acid such as hydrobromic acid in concentration from 10 wt-% to 100 wt-% (100 wt-% corresponds to gaseous hydrogen bromide). Preferably from 48 wt-% to 62 wt-% hydrobromic acid is added and the reaction is provided at temperatures from 20° C. to the reflux preferably from 25 to 30° C. for 30 minutes to 2 hours preferably 1 hour. The mixtures is then cooled to −10 to 5° C. and stirred at −10 to 5° C. for 1 to 2 hours. The obtained hydrobromide salt is isolated by filtration or centrifugation. The olmesartan medoxomil hydrohalide salts can be recrystallised to further purify it, from suitable solvent such as THF, diethyl ether or mixtures thereof, preferably from THF.

Figure 4:
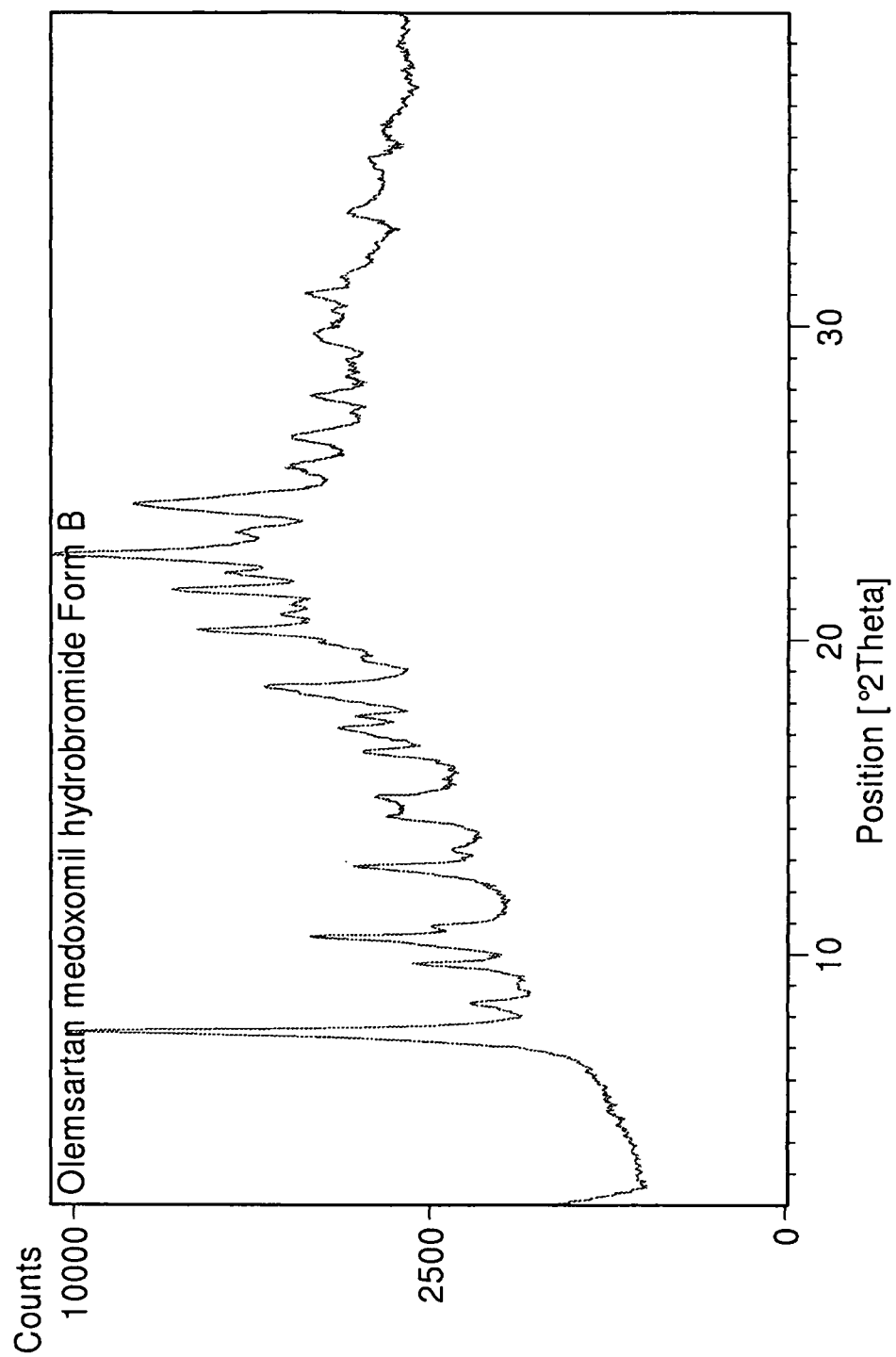
FIG. 4 is an X-ray powder diffraction spectrum of olmesartan medoxomil hydrobromide Form B.
Figure 5:
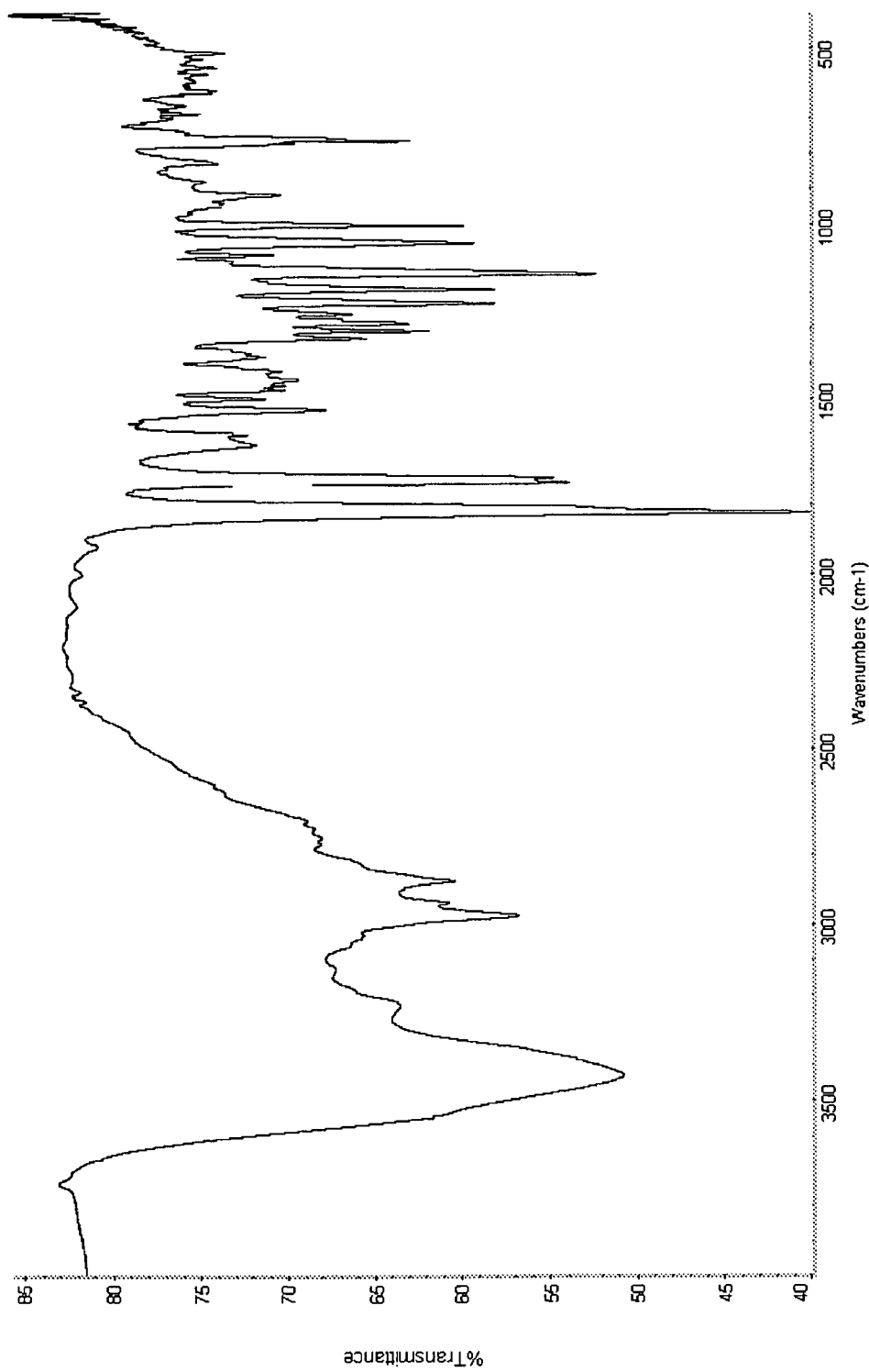
FIG. 5 is an IR spectrum of olmesartan medoxomil hydrobromide Form B.
Figure 6:
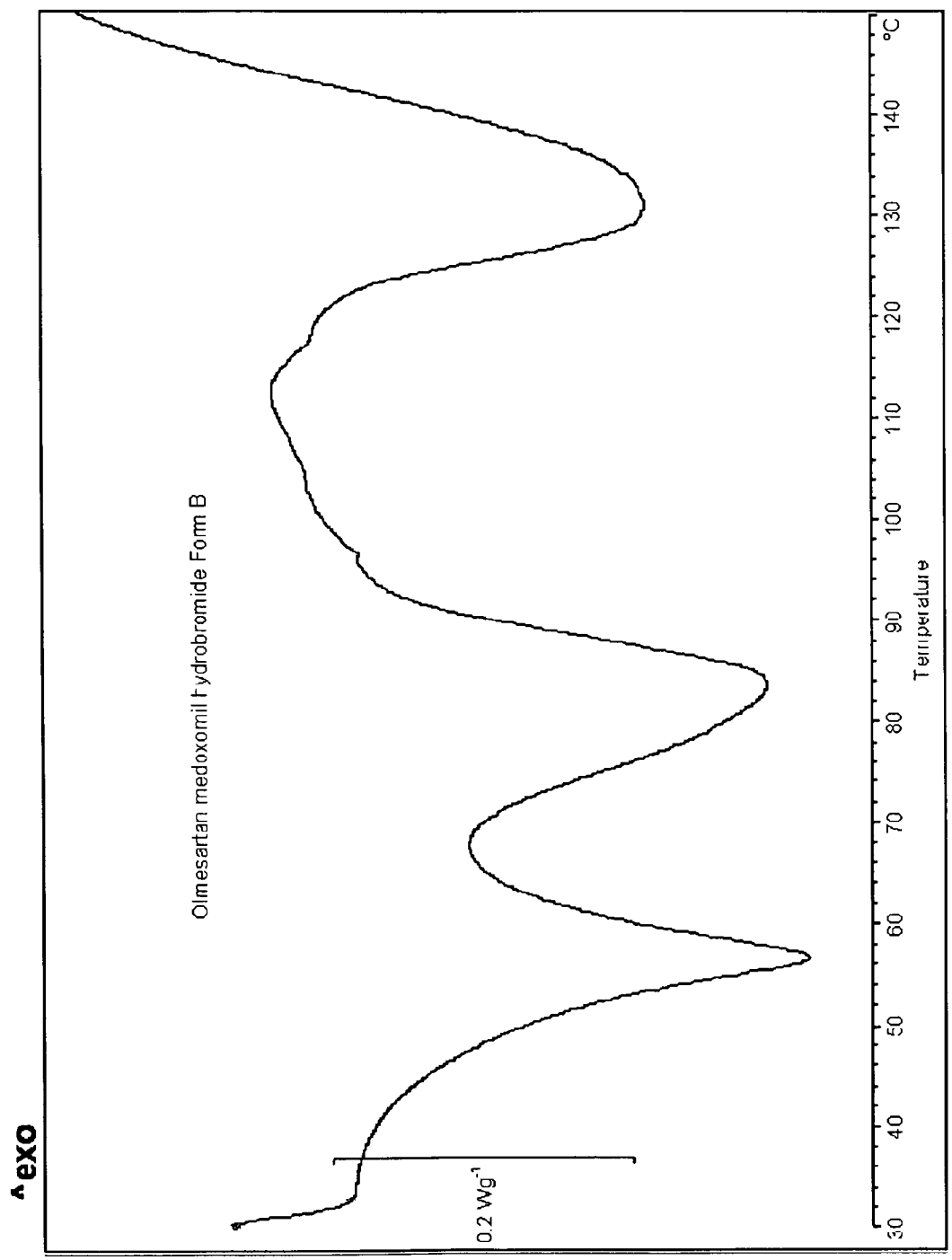
FIG. 6 is a DSC thermogram of olmesartan medoxomil hydrobromide Form B.

Generally olmesartan medoxomil hydrobromide form B is obtained from solutions of olmesartan medoxomil hydrobromide in THF or THF rich mixtures. Preferably olmesartan medoxomil hydrobromide form B is formed upon recrystallisation of olmesartan medoxomil hydrobromide form A from THF. It is characterized by the diffractions in X-ray diffraction pattern substantially as in FIG. 4 at following 2-theta values in particular: 7.5, 10.5, 20.3, 21.6, 22.7, 24.3. It is also characterized by an IR spectrum as in FIG. 5 having representative peaks at about 1145, 922, 831, 768, 704, 690 cm$^{-1}$. It is also characterized by a DSC thermogram as in FIG. 6 showing evident endothermic peak of desolvatation with peak at about 56° C. The endothermic peak at about 83° C. corresponds to melting with decomposition.

Figure 10:
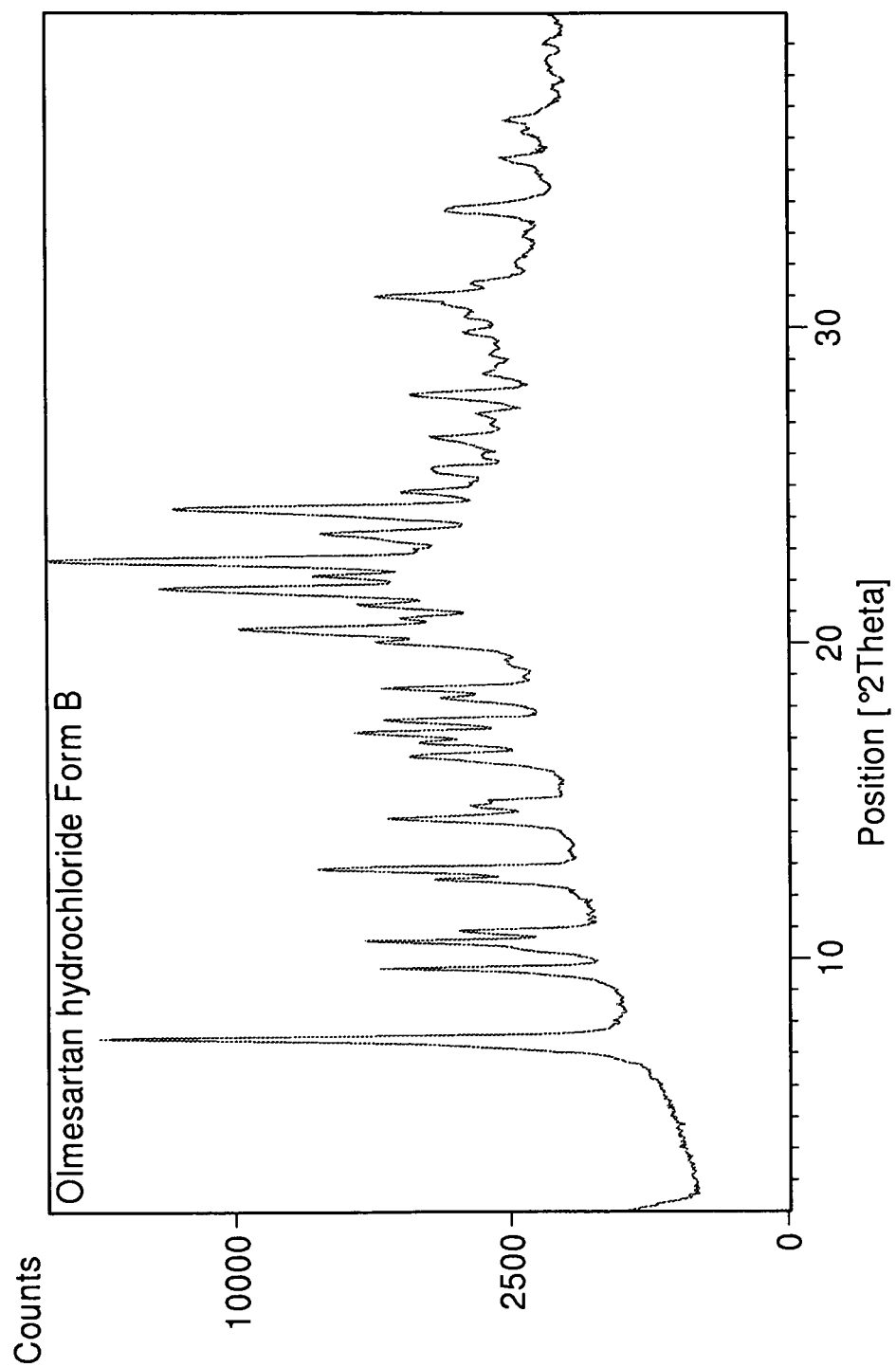
FIG. 10 is an X-ray powder diffraction spectrum of olmesartan medoxomil hydrochloride Form B.
Figure 11:
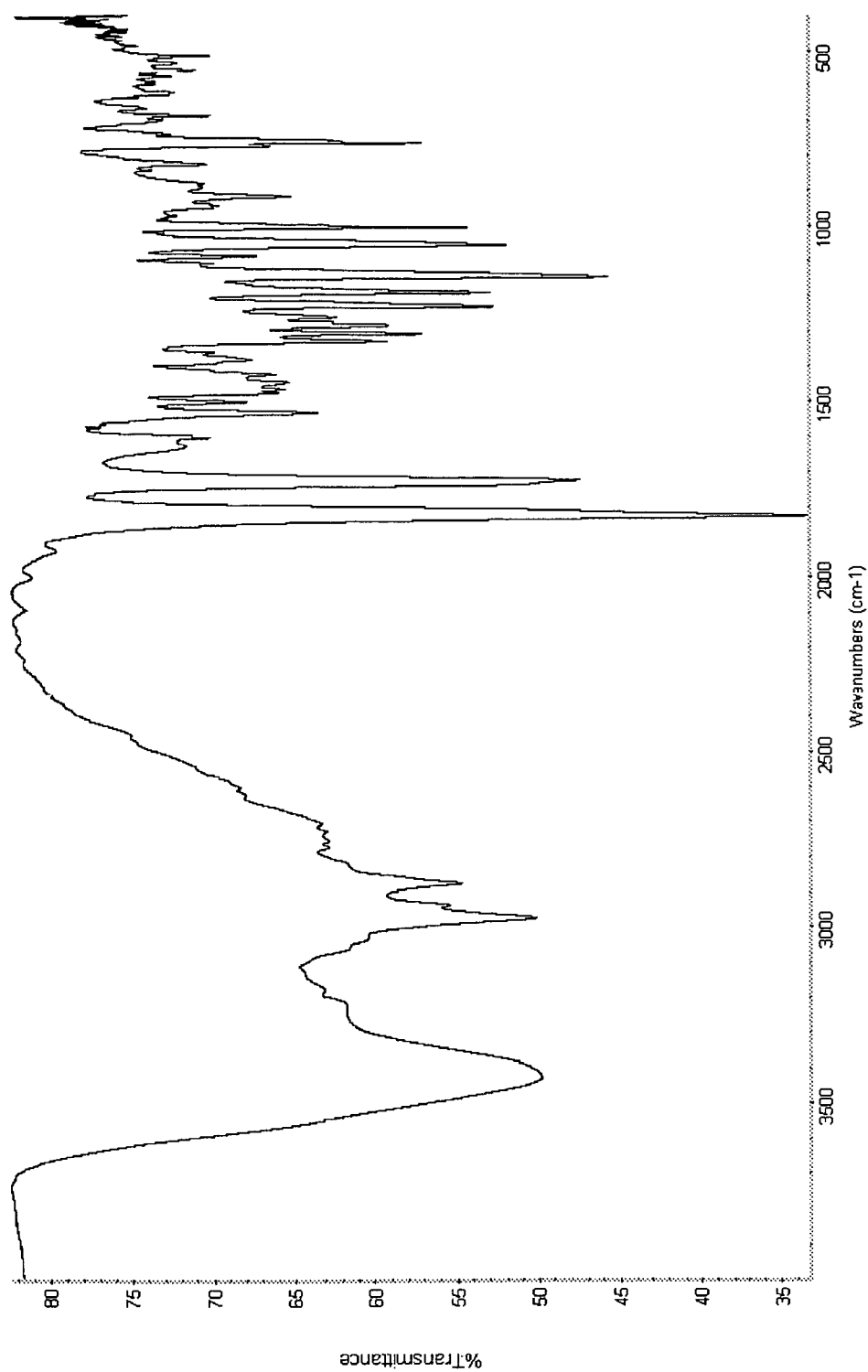
FIG. 11 is an IR spectrum of olmesartan medoxomil hydrochloride Form B.
Figure 12:
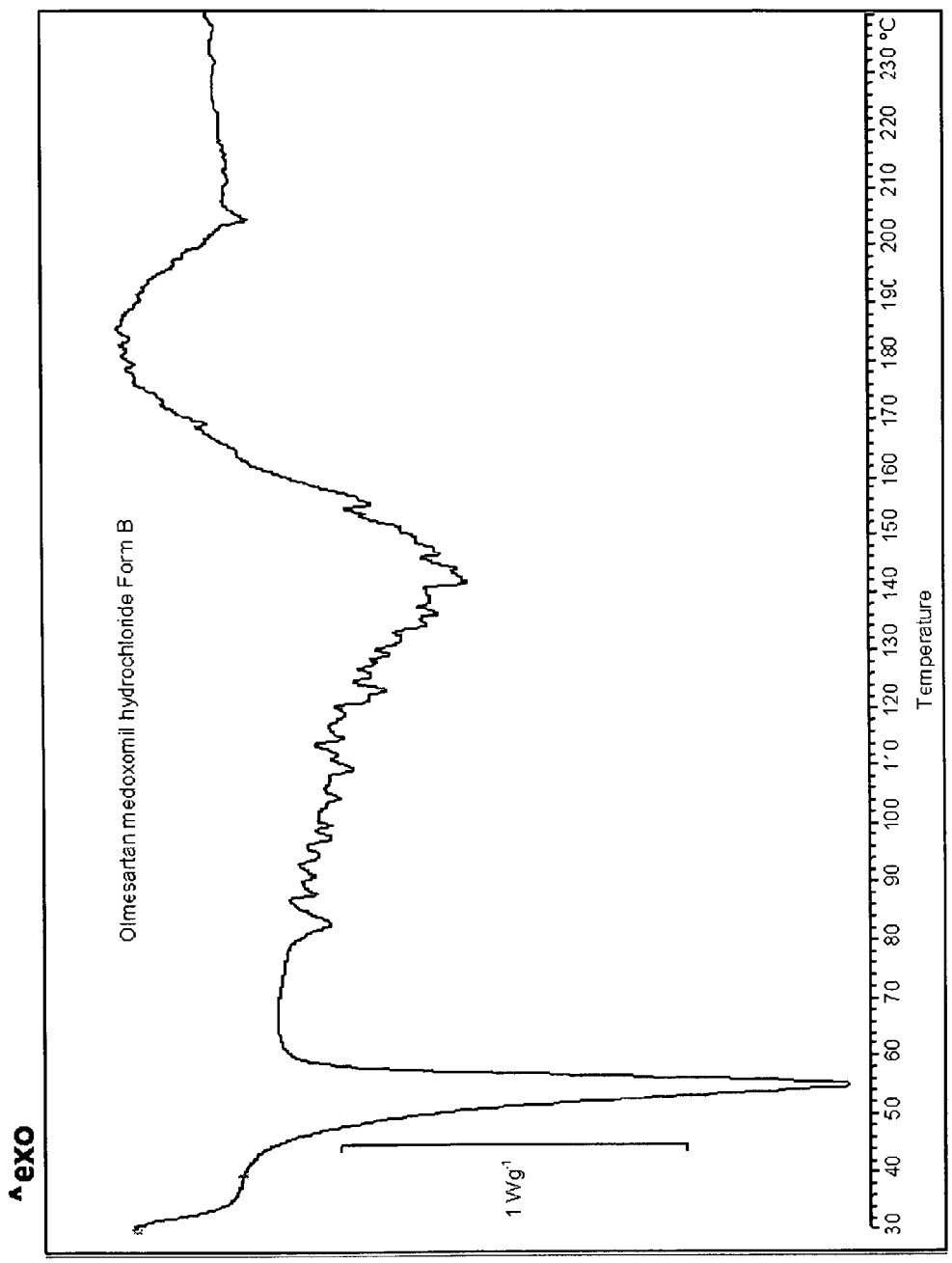
FIG. 12 is a DSC thermogram of olmesartan medoxomil hydrochloride Form B.

Olmesartan medoxomil hydrochloride form B is formed upon recrystallisation of olmesartan medoxomil hydrochloride form A from THF or a mixture of THF and diethyl ether. It is characterized by the diffractions in X-ray diffraction pattern substantially as in FIG. 10 at following 2-theta values in particular: 7.5, 9.7, 12.8, 17.2, 21.7, 22.6. It is also characterized by an IR spectrum as in FIG. 11 having representative peaks at about 1826, 1502, 1386, 1365, 1331, 1145, 1006, 950, 923, 517 cm$^{-1}$. It is also characterized by a DSC thermogram as in FIG. 12 showing characteristic endothermic peak with onset temperature at about 49° C. and peak value of about 54° C. and the enthalpy of desolvatation of about −59 J/g. The solvate decomposes after desolvatation at about 80° C.

Optionally, in either embodiment, in order to convert the olmesartan medoxomil hydrohalide salt to olmesartan medoxomil, the olmesartan medoxomil hydrohalide salt is dissolved in the mixture of at least one water miscible solvent and water. Suitable water miscible organic solvents include, but are not limited to, acetone, acetonitrile, lower alcohols, tetrahydrofuran, 1,4-dioxane, dimethyl sulfoxide, N,N-dimethylformamide, N,N-dimethylacetamide. Alcohols, acetone and acetonitrile are preferred; acetone is the most preferred. The organic solvent to water ratio is preferably between 2:1 and 1:3 by volume, more preferably about 1:2 by volume.

To this solution is added aqueous solution of inorganic base selected from alkali and alkaline earth carbonates, hydrogen carbonates, hydroxides, alkoxides, preferably hydrogen carbonates, more preferably $NaHCO_3$. The amount of base used should be such to raise the pH to about 5 to 8, more preferably 5.5 to 6.5. The temperature of the mixture should be maintained at about 0 to about 30° C., more preferably at about 20 to about 25° C., until olmesartan medoxomil is precipitated, and then at about 0 to about 5° C. to achieve maximum yield.

The precipitated olmesartan medoxomil is collected using any method known in the art, such as centrifugation or filtration.

Optionally olmesartan medoxomil may be recrystallised from a suitable solvent such as acetone, acetonitrile, methanol, ethanol, propanol, 2-propanol, methyl acetate, ethyl acetate, isopropyl acetate, and mixtures thereof or mixtures thereof with water; preferably acetone and acetonitrile, more preferably acetonitrile.

When dissolved in physiological medium, olmesartan medoxomil hydrohalide salts or olmesartan medoxomil obtainable by the process according to the first aspect of the invention behave similarly to olmesartan medoxomil and are expected to exhibit comparable efficiency as antihypertensive, so they can be used to manufacture a pharmaceutical composition; preferably for treating hypertension. Manufacturing of a pharmaceutical composition can be done by using well known methods to a person skilled in pharmaceutical technology. For example, olmesartan medoxomil hydrohalide salts or olmesartan medoxomil obtainable by the process according to the first aspect of the invention are mixed together with pharmaceutically acceptable carrier and optionally further undergo the process of wet granulation, direct compression or the like. Preferably, the so obtained mass gets tableted using a tableting equipment to obtain a tablet comprising olmesartan medoxomil hydrohalide salts or olmesartan medoxomil obtainable by the process according to the first aspect.

EXAMPLES

The following examples are offered to illustrate aspects of the present invention, and are not intended to limit the present invention in any manner.

The purity as used in this specification is determined by HPLC and is defined as ratio of area of olmesartan medoxomil and total area. In particular it can be determined by subjecting the mixture to a chromatography on C18 column and using water/acetonitrile and phosphate buffer (pH 2.5) as eluent.

X-Ray powder diffractograms were recorded with diffractometer X'Pert PRO MPD; CuKα radiation and it is understood that the intensity of the diffraction signals may vary as a function of particle size of the sample or orientation, and that diffractions recorded under different conditions, i.e. different diffractometers may differ for as much as ±0.2° 2-theta, but preferably not more than ±0.1° 2-theta.

IR Spectra were recorded with Nicolet Nexus FT-IR. Melting points were established by Mettler Toledo DSC822.

Example 1

Formation of Olmesartan Medoxomil Hydrobromide Form A

Trityl olmesartan medoxomil (8 g, 10 mmol) is added to a mixture of acetone (35 ml) and water (10 ml). To the resulting suspension 48 wt-% aqueous hydrobromic acid (3.5 ml, 30 mmol) is added. The mixture is then stirred at room temperature for 2 h. Water (130 ml) is added and the mixture is stirred for additional 30 minutes. The precipitated triphenylmethanol is filtered off. The filtrate is concentrated in vacuum at 40° C. to 100 ml, and then stirred vigorously for 1 h at room temperature and then additional 30 minutes at 0° C. The precipitate is filtered to give 4.7 g of olmesartan medoxomil hydrobromide Form A (97.6% area).

Example 2

Formation of Olmesartan Medoxomil Hydrobromide Form B

Olmesartan medoxomil hydrobromide Form A (4.7 g, 97.6% area) is added to THF (80 ml) and the mixture is stirred vigorously for 1 h at room temperature. The precipitate is filtered and washed with small amount of cold THF to give 4.9 g olmesartan medoxomil hydrobromide Form B (99.4% area).

Example 3

Formation of Olmesartan Medoxomil Hydrobromide Form B

Trityl olmesartan medoxomil (8 g, 10 mmol) is dissolved in THF (50 ml) and 48 wt-% aqueous hydrobromic acid (3.5 ml, 30 mmol) is added. The mixture is stirred for 1 hour at room temperature and then 1 hour at 0° C. The precipitate is filtered, washed with cold THF (20 ml) and dried overnight in vacuum at room temperature to give 5.7 g of olmesartan medoxomil hydrobromide Form B (98.6% area).

Example 4

Formation of Olmesartan Medoxomil Hydrobromide Form B

Trityl olmesartan medoxomil (8 g, 10 mmol) is dissolved in THF (25 ml) and diethyl ether (25 ml) and 48 wt-% aqueous hydrobromic acid (3.5 ml, 30 mmol) is added. The mixture is stirred for 1 hour at room temperature and then 1 hour at 0° C. The precipitate is filtered, washed with cold THF (20 ml) and dried overnight in vacuum at room temperature to give 5.0 g of olmesartan medoxomil hydrobromide Form B.

Example 5

Formation of Olmesartan Medoxomil Hydrochloride Form A

Trityl olmesartan medoxomil (8 g, 10 mmol) is added to a mixture of acetone (35 ml) and water (10 ml). To the resulting suspension 37 wt-% aqueous hydrochloric acid (2.5 ml, 30 mmol) is added. The mixture is then stirred at room temperature for 4 h. Water (130 ml) is added and the mixture is stirred for additional 30 minutes. The precipitated triphenylmethanol is filtered off. The filtrate is concentrated in vacuum at 40° C. to 100 ml, and then stirred vigorously for 1 h at room temperature and then additional 30 minutes at 0° C. The precipitate is filtered to give 4.7 g of olmesartan medoxomil hydrochloride Form A (98.3% area).

Example 6

Formation Olmesartan Medoxomil Hydrochloride Form B

Olmesartan medoxomil hydrochloride Form A (5 g, 92.5% area) is added to THF (80 ml) and the mixture is stirred for 30 minutes at room temperature and then 1 hour at 0° C. The precipitate is filtered and washed with small amount of cold THF to give 4.9 g olmesartan medoxomil hydrochloride Form B (99.3% area).

Example 7

Formation of Olmesartan Medoxomil

Olmesartan medoxomil hydrobromide Form B (5.8 g) is added to a mixture of acetone (13 ml) and water (26 ml) and stirred at room temperature to give a clear solution. Saturated aqueous solution of $NaHCO_3$ (5.4 ml) is added slowly with vigorous stirring. The mixture is stirred for 1 hour at room temperature and then 1 hour at 0° C. The product is filtered, washed with cold water and recrystallised from acetonitrile to give 3.3 g olmesartan medoxomil (99.86% area).

Example 8

Formation of Olmesartan Medoxomil

Olmesartan medoxomil hydrochloride Form B (4.9 g) is added to a mixture of acetone (13 ml) and water (26 ml) and stirred at room temperature to give a clear solution. Saturated aqueous solution of $NaHCO_3$ (5.8 ml) is added slowly with vigorous stirring. The mixture is stirred for 1 hour at room temperature and then 1 hour at 0° C. The product is filtered, washed with cold water and recrystallised from acetonitrile to give 3 g olmesartan medoxomil (99.84% area).

Example 9

Formation of Olmesartan Medoxomil

Trityl olmesartan medoxomil (18 g, 22.5 mmol) (95.5% area) is added to a mixture of acetone (68 ml) and water (22 ml). To the resulting suspension 48 wt-% aqueous hydrobromic acid (8.5 ml, 72 mmol) is added. The mixture is then stirred at room temperature for 2 h. Water (180 ml) is added and the mixture is stirred for additional 15 minutes. The precipitated triphenylmethanol is filtered off. The filtrate is concentrated in vacuo at 40° C. to 200 ml and then stirred vigorously for 20 minutes at room temperature and then additional 40 minutes at 0° C. The precipitate is filtered and dried overnight in vacuum at 25° C. to give 12.9 g of olmesartan medoxomil hydrobromide Form A. This was added to THF (150 ml) and the mixture is stirred vigorously for 30 minutes at room temperature and 1 hour at 0° C. The precipitate is filtered and washed with 25 ml of cold THF to give olmesartan medoxomil hydrobromide Form B, which is then dissolved in a mixture of water (100 ml) and acetone (50 ml). To a clear solution saturated aqueous $NaHCO_3$ is added to raise pH to 5.6. The mixture is stirred for 1 hour at room temperature and 2 hours at 0° C. The precipitate is filtered, washed with water and then recrystallised from acetonitrile (87 ml) to give 8.3 g of olmesartan medoxomil (99.74% area).

Example 10

Formation of Olmesartan Medoxomil

Trityl olmesartan medoxomil (250 g, 310 mmol) (97.3% area) is dissolved in THF (1560 ml) and 48 wt-% aqueous hydrobromic acid (70.6 ml, 625 mmol) is added slowly. The mixture is stirred for at 25° C. After 1 hour the precipitate forms. The mixture is stirred for 1 additional hour at 25° C., then cooled to −5° C. and stirred for 1.5 hours at −5° C. The precipitate is filtered. 940 ml of THF is added to the precipitate and the mixture is stirred for 1 h at 25° C. and then 1 hour at −5° C. Then precipitate is filtered off and washed with cold THF (150 ml). It is then dissolved in a mixture of water (875 ml) and acetone (440 ml). To a clear solution 5% aqueous solution of $NaHCO_3$ is added to raise pH to 5.15. The mixture is stirred for 1 hour at room temperature and 1 hour at 0° C. The precipitate is filtered, washed with water and then recrystallised from a mixture of acetonitrile (280 ml) and water (70 ml) to give 124.5 g of olmesartan medoxomil (99.68% area).

The invention claimed is:

1. A process of preparing or purifying olmesartan medoxomil or a hydrohalide salt thereof, the process comprising the steps of:
    a) providing protected olmesartan medoxomil and forming a solution containing the protected olmesartan medoxomil, solvent and hydrohalic acid, thereby removing the protecting group from the olmesartan medoxomil while leaving the protecting group in solution; or
    b) forming a solution containing olmesartan medoxomil and hydrohalic acid; and
    c) forming olmesartan medoxomil hydrohalide salt in solid form and isolating the olmesartan medoxomil hydrohalide salt; and optionally
    d) converting the olmesartan medoxomil hydrohalide salt to olmesartan medoxomil.

2. The process according to claim 1, wherein the hydrohalic acid is hydrochloric acid, hydrobromic acid or hydroiodic acid and the hydrohalide salt in step c) is formed from the hydrohalic acid in step a) or b).

3. The process according to claim 1, wherein the solution containing hydrohalic acid in step a) or b) comprises a mixture of one or more water miscible organic solvents and water, and the water miscible organic solvent is partially or completely removed from the solution to cause formation of olmesartan medoxomil hydrohalide salt in step c).

4. The process according to claim 3, wherein the water miscible organic solvent is selected from the group consisting of a $C_1$ to $C_6$ alcohol, a $C_1$ to $C_6$ ketone, a $C_1$ to $C_6$ nitrile, a $C_1$ to $C_6$ amide, a $C_1$ to $C_6$ ether, dimethyl sulfoxide, or mixtures thereof.

5. The process according to claim 1, wherein the solution containing hydrohalic acid in step a) or b) comprises tetrahydrofuran, and the solution is cooled and/or an antisolvent is added to cause formation of olmesartan medoxomil hydrohalide salt in step c).

6. The process according to claim 1, additionally comprising the step of purifying the olmesartan medoxomil hydrohalide salt obtained in step c) by dissolving it in tetrahydrofuran and forming the olmesartan medoxomil hydrohalide salt by cooling and/or adding an antisolvent to the solution.

7. The process according to claim 1, additionally comprising manufacturing of a pharmaceutical composition.

8. An olmesartan medoxomil hydrohalide salt obtainable by a process according to claim 1.

9. Olmesartan medoxomil hydrobromide form A, having an X-ray diffraction pattern which includes 2-theta values at about: 8.1, 12.6, 13.3, 14.3, 18.9, 25.3, IR spectrum which includes representative peaks at about 1138, 930, 820, 763, 708 cm$^{-1}$, and a melting point with onset of about 81° C. and peak value of about 87° C.

10. Olmesartan medoxomil hydrochloride form A, having an X-ray diffraction pattern which includes 2-theta values at about 10.3, 10.8, 14.9, 16.3, 24.0, 25.4, an IR spectrum which includes representative peaks at about 1819, 1493, 1395, 1380, 1375, 1360, 1333, 1316, 1137, 1010, 940, 918, 878, 526 cm$^{-1}$, a melting point of about 125° C. and a degradation point of about 139° C.

11. Olmesartan medoxomil hydrobromide form B, having an X-ray diffraction pattern which includes 2-theta values at about: 7.5, 10.5, 20.3, 21.6, 22.7, 24.3, an IR spectrum which includes representative peaks at about 1145, 922, 831, 768, 704, 690 cm$^{-1}$, and a DSC thermogram with endothermic peak of desolvatation at about 56° C. and endothermic peak of melting with decomposition at about 83° C.

12. Olmesartan medoxomil hydrochloride form B, having an X-ray diffraction pattern which includes 2-theta values at about 7.5, 9.7, 12.8, 17.2, 21.7, 22.6, an IR spectrum which includes representative peaks at about 1826, 1502, 1386, 1365, 1331, 1145, 1006, 950, 923, 517 cm$^{-1}$, and a DSC thermogram with endothermic peak of desolvatation about 49° C. and endothermic peak of melting with decomposition at about 80° C.

13. A pharmaceutical composition comprising olmesartan medoxomil hydrohalide salt according to any of claims 8 to 12 and a pharmaceutically acceptable carrier.

14. The process according to claim 2, wherein the hydrohalic acid is hydrochloric acid or hydrobromic acid.

15. The process according to claim 14, wherein the hydrohalic acid is hydrobromic acid.

16. The process according to claim 4, wherein the water miscible organic solvent comprises acetone, acetonitrile, ethanol, t-butanol, tetrahydrofuran, or 1,4-dioxane.

17. The process of claim 16, wherein the water miscible organic solvent comprises acetone.

18. A method of treating hypertension comprising administering a hypertension treating effective amount of the pharmaceutical composition of claim 13 to a subject in need thereof.

* * * * *